US012318620B2

(12) United States Patent
Sun et al.

(10) Patent No.: US 12,318,620 B2
(45) Date of Patent: Jun. 3, 2025

(54) LEADLESS PACEMAKER AND TAIL END COMPONENT AND HEAD END COMPONENT THEREOF

(71) Applicant: MICROPORT SOARING CRM (SHANGHAI) CO., LTD., Shanghai (CN)

(72) Inventors: Jiangkai Sun, Shanghai (CN); Grace Jang, Shanghai (CN); Zhijun Cheng, Shanghai (CN)

(73) Assignee: MICROPORT SOARING CRM (SHANGHAI) CO., LTD., Shanghai (CN)

( * ) Notice: Subject to any disclaimer, the term of this patent is extended or adjusted under 35 U.S.C. 154(b) by 553 days.

(21) Appl. No.: 17/786,748

(22) PCT Filed: Dec. 18, 2020

(86) PCT No.: PCT/CN2020/137797
§ 371 (c)(1),
(2) Date: Jun. 17, 2022

(87) PCT Pub. No.: WO2021/121412
PCT Pub. Date: Jun. 24, 2021

(65) Prior Publication Data
US 2023/0050125 A1 Feb. 16, 2023

(30) Foreign Application Priority Data
Dec. 20, 2019 (CN) .......................... 201911328228.2

(51) Int. Cl.
*A61N 1/375* (2006.01)
*A61N 1/362* (2006.01)
*A61N 1/372* (2006.01)

(52) U.S. Cl.
CPC ......... *A61N 1/37512* (2017.08); *A61N 1/362* (2013.01); *A61N 1/37205* (2013.01); *A61N 1/37518* (2017.08); *A61N 1/3756* (2013.01)

(58) Field of Classification Search
None
See application file for complete search history.

(56) References Cited

U.S. PATENT DOCUMENTS 9,216,285 B1 * 12/2015 Boling .............. A61B 5/02444
9,480,850 B2 * 11/2016 Schmidt .............. A61N 1/3756
(Continued)

FOREIGN PATENT DOCUMENTS

CN    101578067 A    11/2009
CN    106794345 A    5/2017
(Continued)

*Primary Examiner* — Kennedy Schaetzle
(74) *Attorney, Agent, or Firm* — Muncy, Geissler, Olds & Lowe, P.C.

(57) ABSTRACT

A leadless pacemaker (100, 200, 300) and trailing (1, 3, 5) and leading (2, 4, 6) components thereof are disclosed. The trailing component (1, 3, 5) includes a first connecting member (12, 32) and a second connecting member (13), and the leading component (2, 4, 6) includes a third connecting member (23, 42, 62) and a fourth connecting member (24, 63). The first connecting member (12, 32) is configured to be detachably connected to the third connecting member (23, 42, 62) and the second connecting member (13) is configured to be detachably or non-detachably connected to the fourth connecting member (24, 63), thereby achieving interlocking between the trailing component (1, 3, 5) and the leading component (2, 4, 6). Additionally, both the first connecting member (12, 32) and the third connecting member (23, 42, 62) are non-biodegradable. At least one of the second connecting member (13) and the fourth connecting member (24, 63) is biodegradable, or the second connecting member (13) is fitted and connected to the fourth connecting (Continued)

member (24, 63) by an associated biodegradable connecting member. Thus, before the connecting member is degraded, it can be ensured that the trailing component (1, 3, 5) and the leading component (2, 4, 6) are firmly connected together by the four connecting members, facilitating overall retrieval or adjustment of the pacemaker (100, 200, 300). Moreover, after the connecting member is degraded, the trailing component (1, 3, 5) can be easily retrieved.

20 Claims, 15 Drawing Sheets

(56) References Cited

U.S. PATENT DOCUMENTS

| | | | |
|---|---|---|---|
| 2004/0147973 A1 | 7/2004 | Hauser | |
| 2011/0270340 A1* | 11/2011 | Pellegrini | A61N 1/0573 607/9 |
| 2012/0109148 A1* | 5/2012 | Bonner | A61N 1/372 606/129 |
| 2013/0125395 A1* | 5/2013 | Pianca | A61N 1/05 29/874 |
| 2015/0306378 A1 | 10/2015 | Schmidt et al. | |
| 2017/0319847 A1 | 11/2017 | Ho et al. | |
| 2018/0207434 A1 | 7/2018 | Webb et al. | |
| 2019/0275340 A1 | 9/2019 | Eby et al. | |
| 2022/0331596 A1* | 10/2022 | Cheng | A61N 1/3752 |

FOREIGN PATENT DOCUMENTS

| | | |
|---|---|---|
| CN | 106823149 A | 6/2017 |
| CN | 207838033 U | 9/2018 |
| CN | 109498207 A | 3/2019 |
| CN | 109498983 A | 3/2019 |
| CN | 109793988 A | 5/2019 |
| CN | 110198759 A | 9/2019 |
| CN | 111001086 A | 4/2020 |

* cited by examiner

LEADLESS PACEMAKER AND TAIL END COMPONENT AND HEAD END COMPONENT THEREOF

TECHNICAL FIELD

The present invention relates to the field of medical devices and, in particular, to a leadless pacemaker and trailing and leading components thereof.

BACKGROUND

Since the advent in 1958, cardiac pacemakers have become a first-line treatment means for bradycardia arrhythmia. With the advancements and innovations over the past more than half century, cardiac pacemaker implantation technology has evolved gradually from the initial form of open chest implantation of single leads for ventricular pacing to the recent form of intravenous implantation of 2-3 leads for atrioventricular physiological pacing or even for biventricular synchronous pacing. However, lead dislodgement, thrombosis, tricuspid regurgitation and lead-related complications have always been handicaps that not only interrupt the normal operation of pacemakers but also seriously threaten patients' health and lives and degrade their quality of life. When a lead-related complication is identified, it is necessary to remove the leads as soon as possible. However, since such lead removal tasks are associated with certain difficulties and risks, they usually must be performed in large electrophysiology centers by dexterous surgeons. This imposes great burden on resource utilization and surgeons' workload. In order to overcome these problems arising from the use of leads, "leadless" cardiac pacemakers have become a new focus of interest in the field of arrhythmia treatment.

Nevertheless, leadless pacemakers are limited in lifespan. For example, in the event of power runout and/or when there is a need to update processing circuitry, it would be desirable to retrieve the entire pacemaker from the heart. However, after a long period of time following implantation (in the chronic phase), it would become impossible to 100% retrieve the leadless pacemaker due to adhesion to or wrapping by myocardial tissue, or entire removal of the leadless pacemaker from myocardial tissue would become difficult and may cause damage to the surrounding cardiac and/or vascular tissue. In some cases, such removal may even cause tears of the myocardial tissue. The retrieval would be particularly difficult in the post-implantation chronic phase due to partial or entire wrapping by tissue.

SUMMARY OF THE INVENTION

It is an object of the present invention to provide a leadless pacemaker and trailing and leading components thereof. The leadless pacemaker is retrievable with less difficulty because of convenient separation of the trailing and leading components from each other.

In order to achieve the above and other related objects, the present invention provides a trailing component of a leadless pacemaker for use with a leading component of the leadless pacemaker. The trailing component includes a first connecting member and a second connecting member.

The first connecting member is configured to be detachably connected to the leading component and the second connecting member is configured to be non-detachably or detachably connected to the leading component, thereby achieving interlocking between the trailing component and the leading component. Additionally, the first connecting member is non-biodegradable and the second connecting member is biodegradable, or the second connecting member is fitted and connected to the leading component by an associated biodegradable connecting member.

Optionally, in the trailing component of a leadless pacemaker, the second connecting member may be configured to be connected to the leading component by a snap fit or by a pinned connection.

Optionally, in the trailing component of a leadless pacemaker, the second connecting member may include a pin hole in alignment with a pin hole in the leading component and adapted for insertion of a biodegradable locating pin therethrough.

Optionally, in the trailing component of a leadless pacemaker, the second connecting member may include a locating snap recess configured to form a snap fit with a protruding snap feature of the leading component. Alternatively, the second connecting member may include a protruding snap feature made of a biodegradable material and configured to form a snap fit with a locating snap recess of the leading component and begin to be degraded a predetermined period of time after the leadless pacemaker is implanted.

Optionally, in the trailing component of a leadless pacemaker, the first connecting member may be configured to be connected to the leading component by a threaded connection, a snap fit or an interference fit.

Optionally, in the trailing component of a leadless pacemaker, the first connecting member may include a guide socket adapted for fitted engagement with a guide stud of the leading component. Alternatively, the first connecting member may include a guide stud adapted for fitted engagement with a guide socket of the leading component.

Optionally, in the trailing component of a leadless pacemaker, the guide socket may have an internal thread. Alternatively, the guide stud may have an external thread.

Optionally, in the trailing component of a leadless pacemaker, the first connecting member may include a locating snap recess configured to form a snap fit with a protruding snap feature of the leading component. Alternatively, the first connecting member may include a protruding snap feature configured to form a snap fit with a locating snap recess of the leading component.

Optionally, in the trailing component of a leadless pacemaker, the trailing component may include a first part and a second part, the first part including a main portion and a recessed portion, the second part disposed over the recessed portion, wherein the second connecting member is provided on the second part, and the second connecting member and/or the second part is/are biodegradable.

Optionally, in the trailing component of a leadless pacemaker, an outer diameter of the second part may be equal to an outer diameter of the main portion.

In order to achieve the above and other related objects, the present invention also provides a leading component of a leadless pacemaker for use with a trailing component of the leadless pacemaker. The leading component includes a third connecting member and a fourth connecting member.

The third connecting member is configured to be detachably connected to the trailing component and the fourth connecting member is configured to be non-detachably or detachably connected to the trailing component, thereby achieving interlocking between the trailing component and the leading component. Additionally, the third connecting member is non-biodegradable and the fourth connecting member is biodegradable, or the fourth connecting member is fitted and connected to the trailing component by an associated biodegradable connecting member.

Optionally, in the leading component of a leadless pacemaker, the fourth connecting member may be configured to be connected to the trailing component by a snap fit or by a pinned connection.

Optionally, in the leading component of a leadless pacemaker, the fourth connecting member may include a pin hole in alignment with a pin hole in the trailing component and adapted for insertion of a biodegradable locating pin therethrough.

Optionally, in the leading component of a leadless pacemaker, the fourth connecting member may include a locating snap recess configured to form a snap fit with a protruding snap feature of the trailing component. Alternatively, the fourth connecting member may include a protruding snap feature made of a biodegradable material and configured to form a snap fit with a locating snap recess of the trailing component and begin to be degraded a predetermined period of time after the leadless pacemaker is implanted.

Optionally, in the leading component of a leadless pacemaker, the third connecting member may be configured to be connected to the trailing component by a threaded connection, a snap fit or an interference fit.

Optionally, in the leading component of a leadless pacemaker, the third connecting member may include a guide socket adapted for fitted engagement with a guide stud of the trailing component. Alternatively, the third connecting member may include a guide stud adapted for fitted engagement with a guide socket of the trailing component.

Optionally, in the leading component of a leadless pacemaker, the guide socket may have an internal thread. Alternatively, the guide stud may have an external thread.

Optionally, in the leading component of a leadless pacemaker, the third connecting member may include a locating snap recess configured to form a snap fit with a protruding snap feature of the trailing component. Alternatively, the third connecting member may include a protruding snap feature configured to form a snap fit with a locating snap recess of the trailing component.

In order to achieve the above and other related objects, the present invention also provides a leadless pacemaker, including:

a trailing component including a first connecting member and a second connecting member; and a leading component configured to be secured to a predetermined object, the leading component including a third connecting member and a fourth connecting member, wherein the first connecting member is detachably connected to the third connecting member and the second connecting member is non-detachably or detachably connected to the fourth connecting member, thereby achieving interlocking between the trailing component and the leading component, and wherein the first and third connecting members are non-biodegradable, and the second connecting member and/or the fourth connecting member biodegradable is/are biodegradable, or the second connecting member is fitted and connected to the fourth connecting member by an associated biodegradable connecting member.

Optionally, in the leadless pacemaker, the first connecting member may be threadedly connected to the third connecting member, wherein the second connecting member is connected to the fourth connecting member by a snap fit, and wherein one of the second and fourth connecting members includes a locating snap recess, and the other of the second and fourth connecting members includes a protruding snap feature, the locating snap recess configured in an annular shape.

Optionally, in the leadless pacemaker, each of the second and fourth connecting members may include a pin hole, and the pin hole in the trailing component is aligned with the pin hole in the leading component, wherein the associated biodegradable connecting member includes a locating pin inserted through both the pin holes of the trailing and leading components and configured to begin to be degraded a predetermined period of time after the leadless pacemaker is implanted.

In the leadless pacemaker and the trailing and leading components thereof provided in the present invention, through designing the leadless pacemaker as two parts, i.e., the trailing and leading components, which are separable after the leadless pacemaker is implanted into the body, implantation, relocation, retrieval and replacement of the leadless pacemaker are made easier. For example, during implantation, the first and second connecting members in the trailing component are fitted and connected to the third and fourth connecting members in the leading component. This allows easy implantation of the entire leadless pacemaker into the body and facilitates relocation of the pacemaker when it is implanted at an undesirable location. In the latter chronic phase, the leadless pacemaker will be partially wrapped by tissue, making retrieval of the entire leadless pacemaker very difficult and possible to cause damage to tissue. In order to overcome this, the second connecting member in the trailing component, the fourth connecting member in the leading component, or the associated connecting member connecting the second connecting member to the fourth connecting member is designed to be biodegraded in this phase. As such, the trailing and leading components can be separated from each other simply by performing an operation to separate the first connecting member from the third connecting member. As a result, the trailing component can be replaced for a new one, or only the trailing component is retrieved, with the less bulky leading component being left in the body. In this way, the non-retrieved part does not take up a significant space in the body, leaving more room for a new leadless pacemaker that may be later implanted.

BRIEF DESCRIPTION OF THE DRAWINGS

The accompanying drawings are provided to facilitate a better understanding of the present invention and do not unduly limit the scope thereof in any sense. In these figures.

Figure 1:
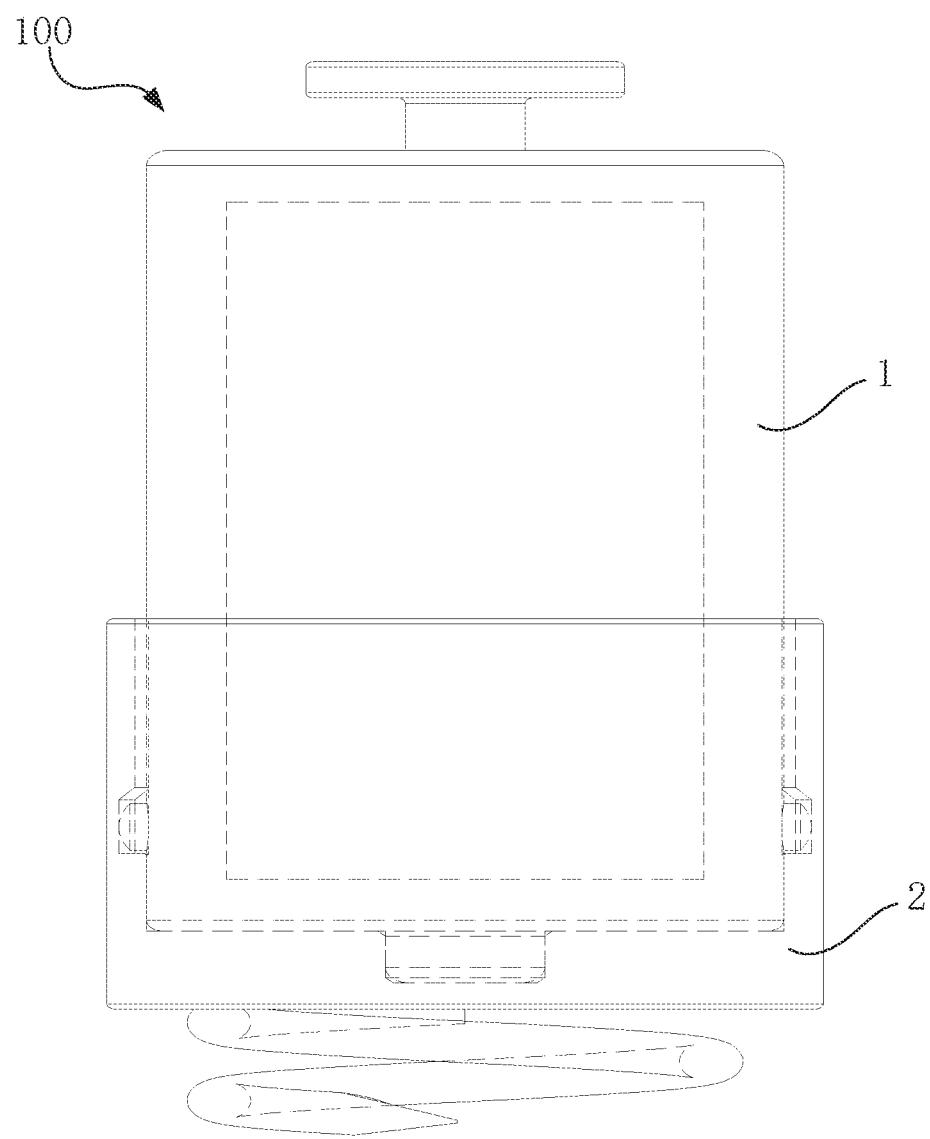
FIG. 1 shows a leadless pacemaker provided in Embodiment 1 of the present invention in an assembled configuration.

REFERENCE NUMERALS USED IN THE FIGURES 100, 200, 300—Leadless Pacemaker;
1, 3, 5—Trailing Component;
11, 31, 511—First Body;
511a—Main Portion; 511b—Recessed Portion;
12, 32—First Connecting Member;
121, 35, 512—Guide Stud;
13—Second Connecting Member;
131—Elastic Fastener;
14—Fifth Connecting Member;
321—Locating Block;
34, 44—Pin Hole;
2, 4, 6—Leading Component;
21, 41, 61—Second Body;
22—Anchoring Mechanism;
23, 42, 62—Third Connecting Member;
231, 45, 621—Guide Socket;
24, 63—Fourth Connecting Member;
241, 421, 631—Locating Snap Recess;
242—Guide Bevel;
243—Guide Groove;
25, 64—Internal Cavity;
26—Proximal End Face;
510—First Part;
510a—First Subpart; 510b—Second Subpart; S1—First Portion; S2—Second Portion;
520—Second Part; 521—Third Body; 522—Barbed Fastener;
400—Locating Sheath;
500—Shrinkable Sheath.

DETAILED DESCRIPTION

Objects, advantages and features of the present invention will become more apparent upon reading the following more detailed description thereof in conjunction with the accompanying drawings. Note that the drawings are provided in a very simplified form not necessarily drawn to exact scale for the only purpose of helping to explain the disclosed embodiments in a more convenient and clearer way.

As used herein, the terms "proximal" and "distal" as well as "leading" and "trailing" are employed to describe relative orientations, relative positions and directions between components of a medical device or actions thereof, as viewed by one operating the device. Without wishing to be limiting, a "proximal" or "leading" end usually refers to an end closer to the operator, and a "distal" or "trailing" end usually refers to an end that enters a patient first, during normal operation of the medical device.

As used in this specification and in the appended claims, the singular forms "a", "an" and "the" include plural referents, unless the context clearly dictates otherwise. As used in this specification and in the appended claims, the term "or" is generally employed in the sense of "and/or", unless the context clearly dictates otherwise. As used in this specification and in the appended claims, the term "plurality" is generally employed in the sense of "two" or "more than two", unless the context clearly dictates otherwise.

It is a primary object of the present invention to provide a leadless pacemaker including a trailing component and a leading component. The trailing component includes a first connecting member and a second connecting member, and the leading component includes a third connecting member and a fourth connecting member. The first connecting member is configured to be detachably connected to the third connecting member, and the second connecting member is configured to be detachably or non-detachably connected to the fourth connecting member, thus achieving interlocking between the trailing and leading components. Additionally, both the first and third connecting members are non-biodegradable, while at least one of the second and fourth connecting members is biodegradable. Alternatively, the second connecting member is fitted and connected to the fourth connecting member by an associated biodegradable connecting member.

Accordingly, before the leadless pacemaker is implanted, the trailing and leading components are assembled outside the body so that they are fixedly connected together by means of the four connecting members. The entire leadless pacemaker is then delivered into the body using a delivery device. After the leadless pacemaker of the present invention is implanted into the body, it may encounter the following two major situations.

Situation 1: it is necessary to change the position of the leadless pacemaker during implantation or retrieve the leadless pacemaker within the acute phase (e.g., within 6 months following the implantation). In this situation, the delivery device may be utilized to manipulate the entire leadless pacemaker to detach the leading component from myocardial tissue, thus allowing the leadless pacemaker to be adjusted in location or entirely retrieved. Moreover, in this situation, since the one or two biodegradable ones of the second and fourth connecting members or the associated biodegradable connecting member that connects the second and fourth connecting members together has or have not yet begun to degrade, the entire leadless pacemaker remains in a consolidated state where the trailing and leading components are not separated from each other. This facilitates the entire retrieval or adjustment of the leadless pacemaker.

Situation 2: In the post-operative chronic phase (e.g., after 6 months following the implantation), the one or two biodegradable ones of the second and fourth connecting members or the associated biodegradable connecting member that connects the second and fourth connecting members together begin(s) to degrade and will finally release the interlocking of the trailing and leading components at a later time. Following this, the leading component may be secured and maintained stationary using the delivery device, and the trailing component may be then manipulated using the delivery device to separate the trailing and leading components from each other. At this point, only the trailing component may be retrieved, with the leading component being left in the heart. In this situation, as needed at a later time, the delivery device may be again used to implant a new trailing component into the body and bring it into engagement with the aforesaid leading component, thus allowing replacement of the leadless pacemaker. Alternatively, a new leadless pacemaker may be entirely implanted into the body for replacement.

The above operations can accomplish leadless pacemaker retrieval at less difficulty, particularly in the chronic phase and causing less damage to the surrounding cardiac and/or vascular tissue, providing improved surgical safety. It would be appreciated that, in the chronic phase, the leadless pacemaker is partially or even entirely wrapped by tissue, making entire retrieval of the leadless pacemaker extremely difficult and easy to cause damage to tissue. In view of this, retrieving only the trailing component and leaving the less bulky leading component within the body can reduce damage to tissue. Moreover, the non-retrieved part does not take up a significant space in the body, leaving more room for a new leadless pacemaker that may be implanted subsequently. Additionally, the degradation of the connecting member(s) in the chronic phase can ease separation of the trailing and leading components from each other, making retrieval of the leadless pacemaker even easier. Furthermore, since the unlocking process does not involve the use of any significant mechanical force, the separation will cause only minor damage to the surrounding cardiac and/or vascular tissue, providing improved retrieval safety.

The leadless pacemaker and its trailing and leading components proposed in the present invention will be further described with reference to the accompanying drawings and to specific examples.

Embodiment 1

FIG. 1 shows a leadless pacemaker according to Embodiment 1 of the present invention in an assembled configuration. As shown in FIG. 1, the leadless pacemaker 100 of the present embodiment includes a trailing component 1 and a leading component 2. These two components are assembled together by associated connecting members. In practical use, the trailing component 1 preferably includes various electronic elements (e.g., arranged in the region indicated by the dashed box in FIG. 1) including, but not limited to, a pulse generator, a power supply, a memory, a processor, sensing circuitry, etc. Since these electronic elements in the pacemaker are well known to those skilled in the art and, therefore, need not be described in further detail herein. Additionally, the leading component 2 is configured to anchor to myocardial tissue, and the present invention is not limited to any particular method of anchoring.

Figure 2:
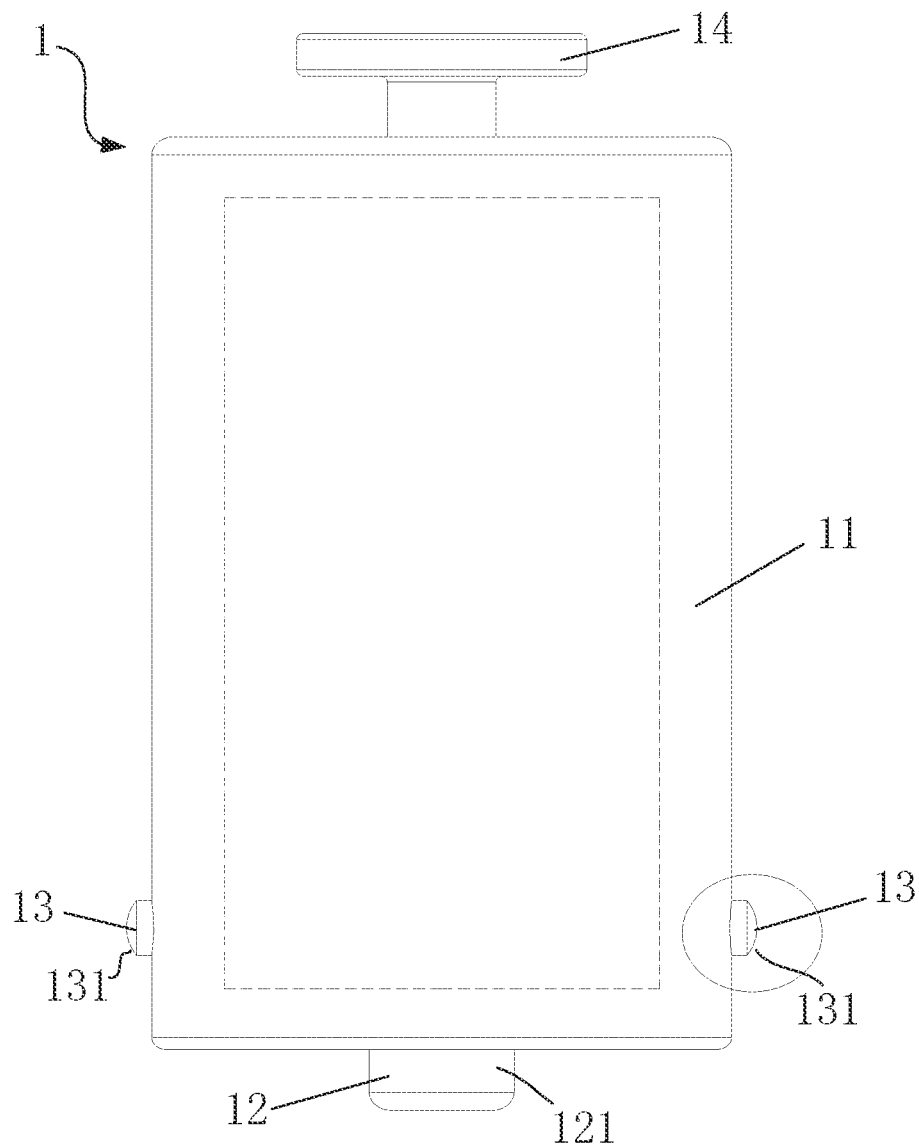
FIG. 2 is a schematic diagram showing the structure of a trailing component in Embodiment 1 of the present invention.
Figure 3A:
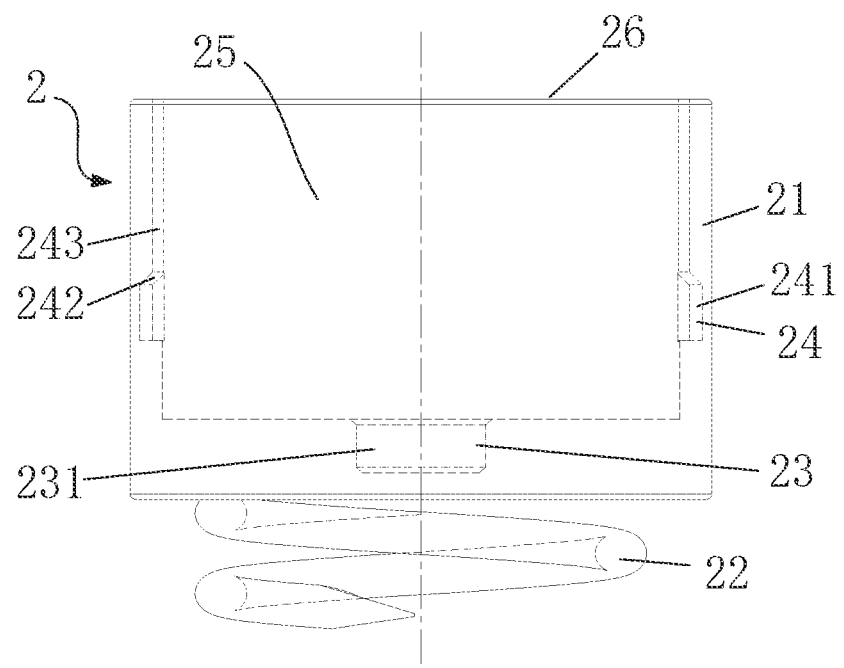
FIG. 3a is a schematic diagram showing the structure of a leading component in Embodiment 1 of the present invention.

FIG. 2 is a schematic diagram showing the structure of the trailing component in Embodiment 1 of the present invention. FIG. 3a is a schematic diagram showing the structure of the leading component in Embodiment 1 of the present invention. As shown in FIG. 2, the trailing component 1 includes a first body 11, the first body 11 is implemented as a housing for accommodating the aforesaid various electronic elements therein. As shown in FIG. 3a, the leading component 2 includes a second body 21, the second body 21 may be implemented as, but is not limited to, a housing. The leading component 2 further includes an anchoring mechanism 22 which is arranged at a distal end of the second body 21 and configured to anchor to myocardial tissue. However, the present invention is not limited to any particular structure of the anchoring mechanism 22. For example, the anchoring mechanism 22 is not limited to the shown helical structure and may alternatively be a wing-shaped or another structure.

With continued reference to FIG. 2, the trailing component 1 further includes a first connecting member 12 and a second connecting member 13, both provided on the first body 11. In this embodiment, the first connecting member 12 includes a guide stud 121, the guide stud 121 is disposed at a distal end of the first body 11, preferably, at a center of the distal end. The second connecting member 13 includes a protruding snap feature implemented preferably as an elastic fastener 131, the elastic fastener 131 projects from an outer wall of the first body 11 outwardly in a direction preferably perpendicular to an axis of the first body 11.

With continued reference to FIG. 3a, leading component 2 further includes a third connecting member 23 and fourth connecting member 24, both provided on the second body 21. In this embodiment, the second body 21 defines an internal cavity 25 that is open proximally, and the third connecting member 23 includes a guide socket 231, the guide socket 231 is arranged at a center of the bottom of the internal cavity 25 (i.e., at a distal end thereof). Additionally, the fourth connecting member 24 includes a locating snap recess 241, the locating snap recess 241 is provided on a side wall of the internal cavity 25.

With combined reference to FIG. 1, in a practical assembly process, the trailing component 1 is inserted distally into the proximally open internal cavity 25 of the leading component 2. During this insertion process, the elastic fastener 131 elastically snaps into the locating snap recess 241, and at the same time, the guide stud 121 engages into the guide socket 231, for example, by an interference fit or a snap fit, thus firmly locking the trailing component 1 and the leading component 2 together. However, the elastic fastener 131 is not limited to being provided on the outer wall of the first body 11, as it may be alternatively provided on an inner wall of the first body 11. For example, like the second body 21, the first body 11 may define a distally open cavity, and the elastic fastener 131 may be provided on a side wall of this cavity. Similarly, the locating snap recess 241 is not limited to being provided on the side wall of the internal cavity 25 of the second body 21. Alternatively, like the first body 11, the locating snap recess 241 may be concave inwardly and provided in an outer wall of the second body 21. In this case, the locking can be achieved simply by inserting the leading component 2 proximally into the cavity. Thus, the present invention is limited to neither any particular location of the elastic fastener 131 on the first body 11 nor any particular location of the locating snap recess 241 on the second body 21. Further, in an alternative embodiment, it is also possible to provide the locating snap recess on the second connecting member 13 and correspondingly the protruding snap feature on the fourth connecting member. For example, the elastic fastener 131 is provided on the second body 21, and the locating snap recess 241 is provided on the first body 11. Therefore, as long as one of the first body 11 and the second body 21 is provided with the elastic fastener 131 and the other with the locating snap recess 241 that is engageable with the elastic fastener 131, one skilled in the art can appropriately configure them.

In an alternative embodiment, the first connecting member 12 includes the guide socket 231, and the third connecting member 23 includes the guide stud 121. Specifically, the guide stud 121 may be provided on the second body 21, and the guide socket 231 on the first body 11. Conveniently, one of the first body 11 and the second body 21 may be provided with the guide stud 121 and the other with the guide socket 231 in cooperation with the guide stud 121. The arrangement of the guide stud 121 on the second body 21 is essentially the same as its arrangement on the first body 11, except for that it is provided at the proximal end of the second body 21 and the guide socket at the distal end of the first body 11. It is to be noted that connection strength between the guide stud 121 and the guide socket 231 needs to exceed the weight of the trailing component 1, in order that after the second connecting member 13 and the fourth connecting member 24 are biodegraded and loses their retaining capabilities, the guide stud 121 and the guide socket 231 will be separated from each other only when subject to an external force, thus ensuring connection reliability.

In some embodiments, an electrical connection is established between the guide stud 121 and the guide socket 231 when they are brought into engagement with each other, enabling transmission of electrical signals and energy between the trailing component 1 and the leading component 2. However, the guide stud 121 and the guide socket 231 may also be non-conductive, and transmission of electrical signals and energy between the trailing component 1 and the leading component 2 may be accomplished in another way. For example, an electrical connection may be directly established when the elastic fastener 131 snaps into the locating snap recess 241. This can achieve the same effect. As another example, the trailing component 1 and the leading component 2 may be electrically connected to each other by means of connecting electrodes provided on corresponding locations of the internal cavity 25 and the first body 11.

The structure and usage of the leadless pacemaker 100 will be further described below in the exemplary context of the first body 11 being provided with the elastic fastener 131 and the guide stud 121 and of the second body 21 being provided with the locating snap recess 241 and the guide socket 231. However, one skilled in the art would be able to adapt the following description to make it suitable for use in the scenario where the second body 21 is provided with the elastic fastener 131 and the guide stud 121 and the first body 11 with the locating snap recess 241 and the guide socket 231.

With continued reference to FIG. 2, in the present embodiment, at least one elastic fastener 131 is so arranged to project from the outer wall of the first body 11. Preferably, two elastic fasteners 131 are arranged in symmetry with respect to the axis of the first body 11. It would be appreciated that the elastic fastener 131 can elastically deform and will be compressed under the action of an external force so as to be separable from or engageable with a locating snap recess 241, thus achieving locking or unlocking. Thus, the elastic fasteners are easy to use while providing good connection reliability. Moreover, with continued reference to FIG. 3a, at least one locating snap recess 241 is provided in the internal cavity 25 of the second body 21. Preferably, two locating snap recesses 241 are arranged in symmetry with respect to an axis of the second body 21. Cooperation of the elastic fastener 131 with the locating snap recess 241 locks the trailing component 1 and the leading component 2 against each other. Moreover, cooperation of the guide stud 121 with the guide socket 231 further ensures that, after the elastic fastener 131 is degraded, the trailing component 1 remains interlocked with the leading component 2 without the risk of disengagement. Preferably, in this embodiment, the elastic fastener 131 is made of a biodegradable material which enables its degradation to begin in the post-operative chronic phase. Moreover, after its degradation has completed, since the guide stud 121 and the guide socket 231 remain in engagement with each other, the trailing component 1 can be separated from the leading component 2 simply by applying opposite forces to them and become retrievable in the chronic phase. However, prior to the degradation of the elastic fastener 131, the entire leadless pacemaker 100 is in an overall consolidated configuration and can therefore be retrieved or adjusted as a whole.

Additionally, the elastic fastener 131 includes a columnar body, preferably a cylindrical body, and is connected to the outer wall of the first body 11. Moreover, a top surface of the columnar body is preferred to be an arc-shaped surface, which helps improve radial stressing and deformation of the elastic fastener 131, thus facilitating the elastic fastener 131's locking and unlocking and ensuring that it will not experience displacement even when axially stressed and provides high connection reliability.

Figure 3B:
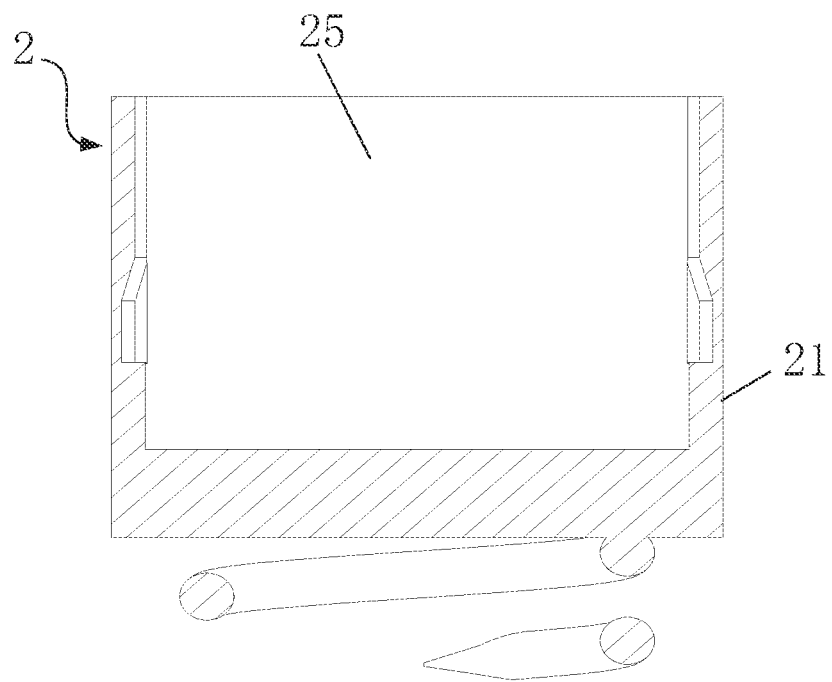
FIG. 3b is an axial cutaway view of the leading component not including a guide socket in Embodiment 1 of the present invention.
Figure 3C:
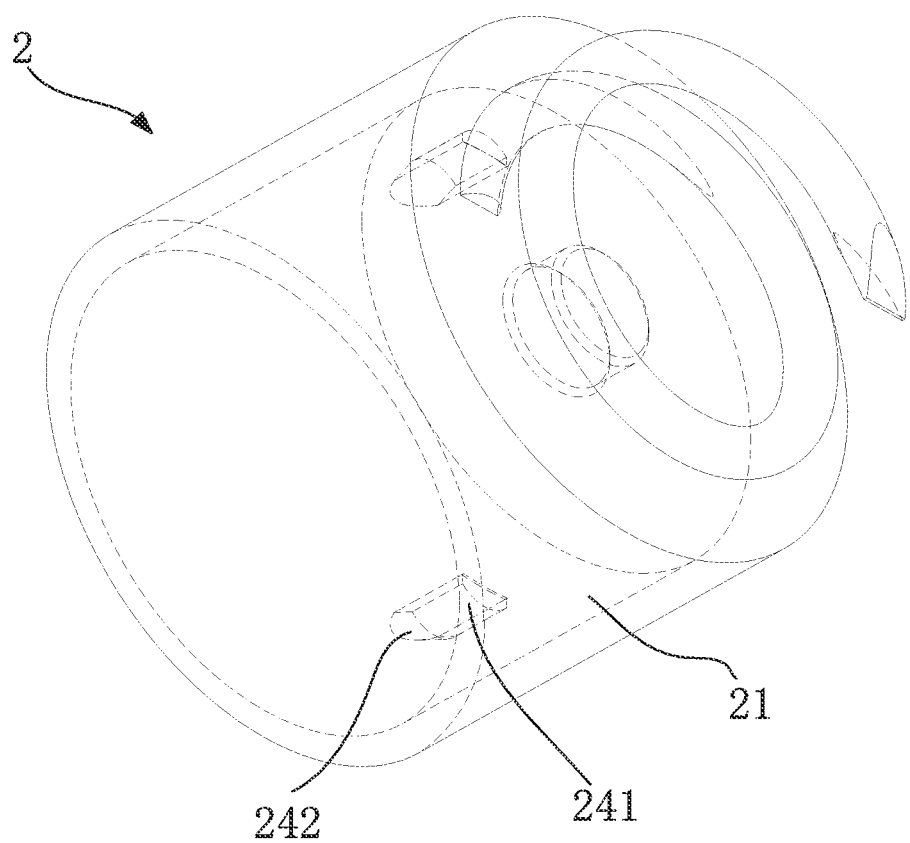
FIG. 3c is a schematic diagram showing the structure of the leading component not including a guide groove in Embodiment 1 of the present invention.

Referring to FIG. 3a, in this embodiment, the locating snap recess 241 is preferably provided at one end with a guide bevel 242, which is preferred to be a curved surface (e.g., an arc-shaped surface) and configured to be brought into conforming contact with the top surface with the elastic fastener 131, thus reducing resistance that the elastic fastener 131 and the locating snap recess 241 encounter during their disengagement and engagement. Preferably, an axially extending guide groove 243 configured to guide movement of the elastic fastener 131 therein into the locating snap recess 241 is provided at the end of the guide bevel 242 away from the locating snap recess 241. This arrangement enables more convenient assembly with higher accuracy. However, in other embodiments, as shown in FIG. 3c, it is also possible to provide only the guide bevel 242 and the locating snap recess 241 but not the guide groove 243.

Thus, in this embodiment, by elastically snapping the elastic fastener 131 into the locating snap recess 241, it can be ensured that the trailing component 1 and the leading component 2 will not disengage from each other when the entire leadless pacemaker 100 is being manipulated. Therefore, the leadless pacemaker 100 can be adjusted in implantation position or entirely retrieved in the acute phase simply by turning it until the anchoring mechanism 22 at the distal end of the leading component 2 is detached from myocardial tissue. However, when in the chronic phase, the majority or entirety of the leadless pacemaker 100 is wrapped by tissue, making it difficult to be retrieved. In order to reduce the difficulty of retrieval, the elastic fastener 131 is configured as a biodegradable structure, which when biodegraded will unlock the elastic fastener 131 from the locating snap recess 241. At this point, despite that the pacemaker is mostly or entirely wrapped by tissue, in order to ensure reliable use, the trailing component 1 is still retained by cooperation between the guide stud 121 and the guide socket 231, and a physician can separate it from the leading component 2 simply by manipulating it using the delivery device. After the separation, the trailing component 1 is retrieved from the body, while the leading component 2 is left therein. Subsequently, as needed, a new trailing component 1 can be implanted in the body and optionally engaged with the leading component 2 left therein. However, in general cases, this leading component 2 would have now become very difficult to be precisely located (due to being wrapped by tissue). When this happens, optionally, a new leadless pacemaker 100 may be instead implanted for complete replacement.

To this end, the elastic fastener 131 is made of a biodegradable material, in the present embodiment, the elastic fastener 131 is configured to begin to degrade a predetermined period of time after the leadless pacemaker 100 is implanted into the body. In general, the chronic phase starts about 6 weeks after the implantation of the leadless pacemaker. Accordingly, the elastic fastener 131 is preferably configured to begin to be degraded 6 weeks after the leadless pacemaker 100 is implanted and take about one year to be completely degraded. When the elastic fastener 131 is completely degraded, it will lose all the physical properties and have no constraint on the locating snap recess 241 at all. The degradation time depends on a number of factors including the molecular weight, crystallinity and hydrophilicity of the material used, the volumes and surface areas of the various components, environmental factors, etc. One skilled in the art may choose appropriate start and finish times of the degradation as actually needed. In embodiments of the present invention, the biodegradable material is selected from polymer materials for medical use, including but not limited to, polylactic acid (PLA), poly-L-lactic acid (PLLA), poly-D-lactic acid (PDLA). Alternatively, it may be PLGA (a random copolymer of L-lactide and glycolide) or PDLGA (a random copolymer of DL-lactide and glycolide). Of course, one skilled in the art may choose a different biodegradable material as practically required, and the present invention is not limited to any particular biodegradable material.

In the present embodiment, the second body 21 is distally connected to a pacing electrode and/or a sensing electrode. In one embodiment, the anchoring mechanism 22 may surround the electrode(s) in a central channel defined by the helical structure. In an alternative embodiment, the helical structure may be part of the electrode(s). In addition, either or both of the first body 11 and the second body 21 may be provided on the outer surface with an annular electrode for sensing myocardial tissue. Further, the first body 11 is preferably provided at the proximal end with a fifth connecting member 14. As shown in FIG. 2, the fifth connecting member 14 is configured to be detachably connected to a shrinkable sheath in the delivery device, thus allowing the trailing component and the entire leadless pacemaker to be manipulated using the shrinkable sheath. However, the present invention is not limited to any particular method of connection between the fifth connecting member 14 and the shrinkable sheath. For example, the connection may be accomplished threadedly, by a snap fit or in another manner that allowing quick attachment and detachment.

Additionally, in an alternative embodiment, the guide stud and the guide socket may not be provided. As shown in FIG. 3b, for example, when the elastic fastener 131 and the locating snap recess 241 can be electrically connected to each other, themselves, the guide stud 121 and the guide socket 231 may not be provided. Instead, at least two sets of elastic fasteners are optionally provided on the first body 11. Each set of elastic fasteners includes two elastic fasteners arranged in symmetry. Therefore, at least four elastic fasteners are spaced from one another about the axis of the first body 11. The elastic fasteners in one set are configured to be biodegradable, while those in the other set are non-biodegradable. As such, when not in the chronic phase, the two sets of elastic fasteners can lock the trailing component 1 and the leading component 2 against each other. However, in the chronic phase, the elastic fasteners in one set is degraded, while those in the other set remain connecting the trailing component 1 to the leading component 2. Similarly, retrieval can be accomplished simply by retaining the leading component 2 with the delivery device and then manipulating the trailing component 1 to separate it from the leading component 2. In this case, according to some embodiments, the first and second connecting members are both elastic fasteners, and the third and fourth connecting members are both locating snap recesses. According to some other embodiments, the first connecting member is an elastic fastener, and the second connecting member is a locating snap recess. Moreover, the third connecting member is a locating snap recess, and the fourth connecting member is an elastic fastener. According to still some other embodiments, the first connecting member is a locating snap recess, and the second connecting member is an elastic fastener. Moreover, the third connecting member is an elastic fastener, and the fourth connecting member is a locating snap recess. Obviously, for the first and second connecting members, it is possible that both of them are elastic fasteners or locating snap recesses and that one of them is an elastic fastener and the other is a locating snap recess. Likewise, for the third and fourth connecting members, it is possible that both of them are elastic fasteners or locating snap recesses and that one of them is an elastic fastener and the other is a locating snap recess.

Figure 10:
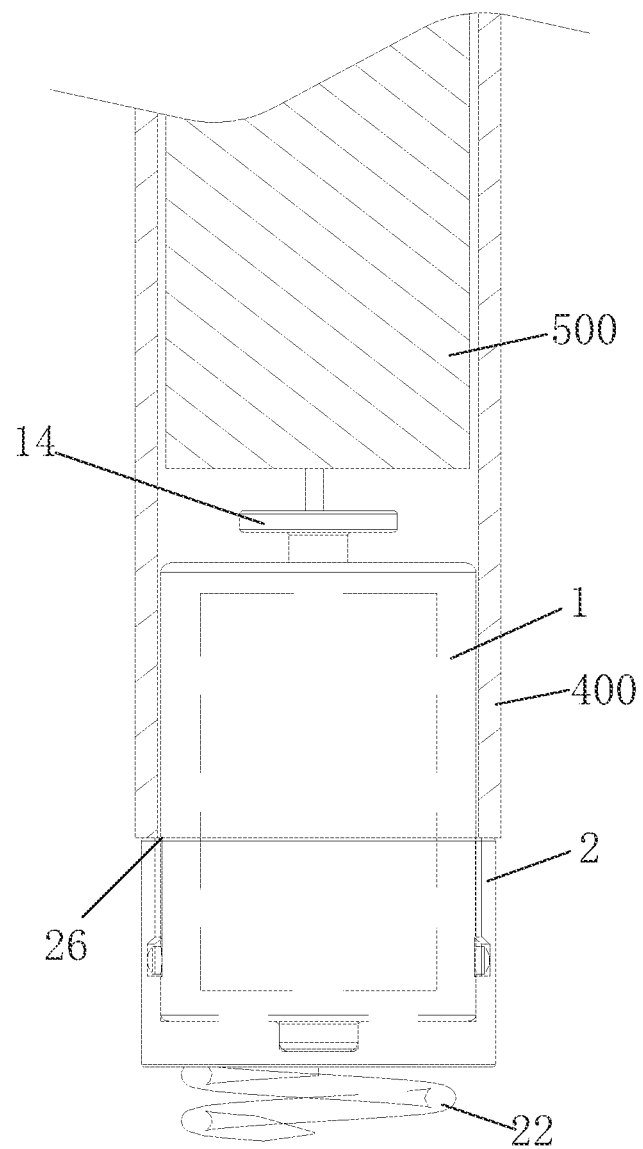
FIG. 10 schematically illustrates trailing component retrieval in the chronic phase according to embodiments of the present invention.

Furthermore, referring to FIG. 3a, in conjunction with FIG. 10, an end face 26 of the second body 21 of the leading component 2 at the proximal end defines a limiting feature configured for positioning of a locating sheath 400 in the delivery device. In this embodiment, the proximal end face 26 is configured to abut against a distal end of the locating sheath 400, thus defining a limit position for distal advancement of the locating sheath 400. As such, the locating sheath 400 surrounds only the trailing component and is able to hold the leading component stationary during separation of the trailing component from the leading component. Preferably, an outer diameter of the second body 21 of the leading component 2 is greater than an inner diameter of the locating sheath 400.

Embodiment 2

This embodiment provides a leadless pacemaker 200, which is essentially similar in structure to that of Embodiment 1. In the following, only differences between them are described.

Figure 4:
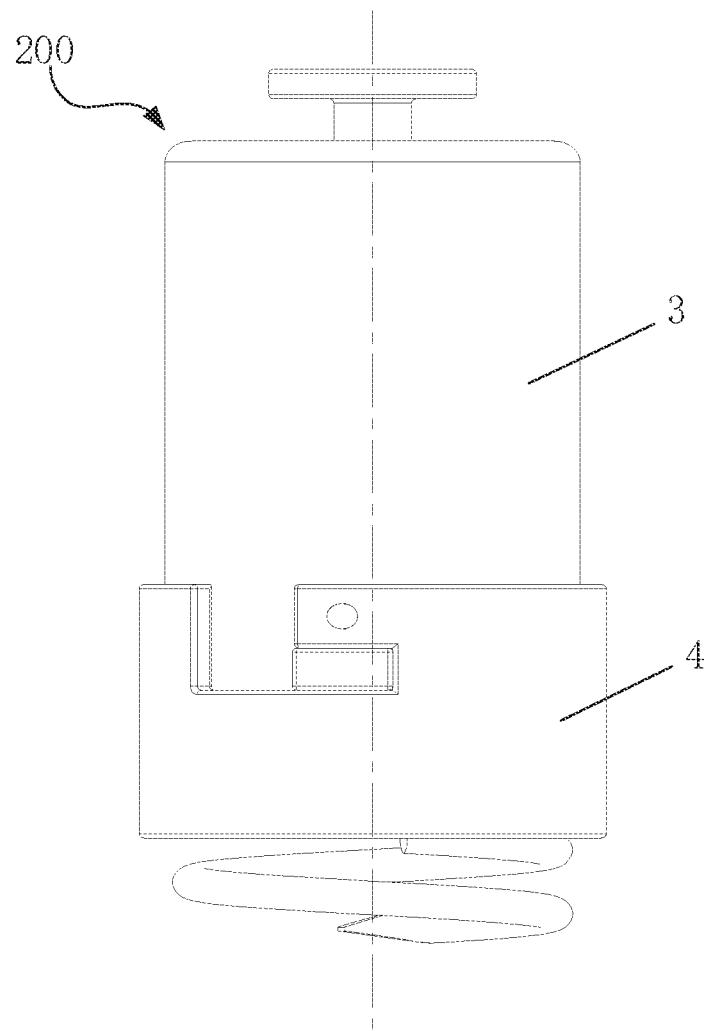
FIG. 4 shows a leadless pacemaker provided in Embodiment 2 of the present invention in an assembled configuration.

FIG. 4 shows the leadless pacemaker of Embodiment 2 of the present invention in an assembled configuration. As shown in FIG. 4, the leadless pacemaker 200 in the present embodiment of the present invention includes a trailing component 3 and a leading component 4, which are detachably connected by a snap fit between a first connecting member 32 and a third connecting member 42. Moreover, a second connecting member is fitted and connected to a fourth connecting member by an associated biodegradable connecting member. Specifically, the second and fourth connecting members are connected together by a pin.

Figure 5A:
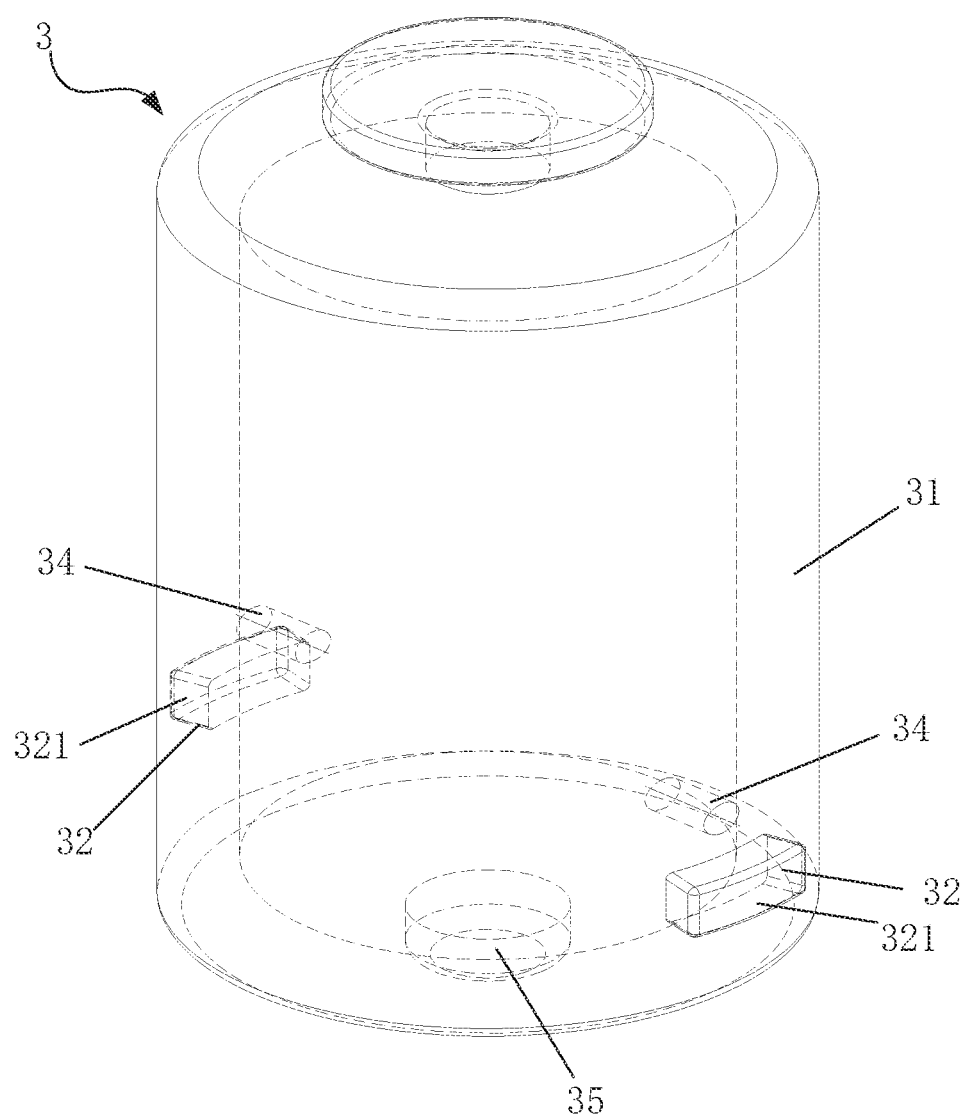
FIG. 5a is a schematic diagram showing the structure of a trailing component including a guide stud in Embodiment 2 of the present invention.

As shown in FIG. 5a, the trailing component 3 includes a first body 31 and, both disposed on the first body 31, the first connecting member 32 and the second connecting member. In this embodiment, the first connecting member 32 includes a protruding snap feature implemented, for example, as a locating block 321 (a rigid fastener which hardly deforms under stress). The locating block 321 extends outwardly from an outer wall of the first body 31 in a direction preferably perpendicular to an axis of the first body 31. The second connecting member includes a pin hole 34 configured to be aligned with a pin hole 44 in the leading component and allow a locating pin to be inserted therethrough. The pin hole 34 radially extends through the outer wall of the first body 31.

Figure 6A:
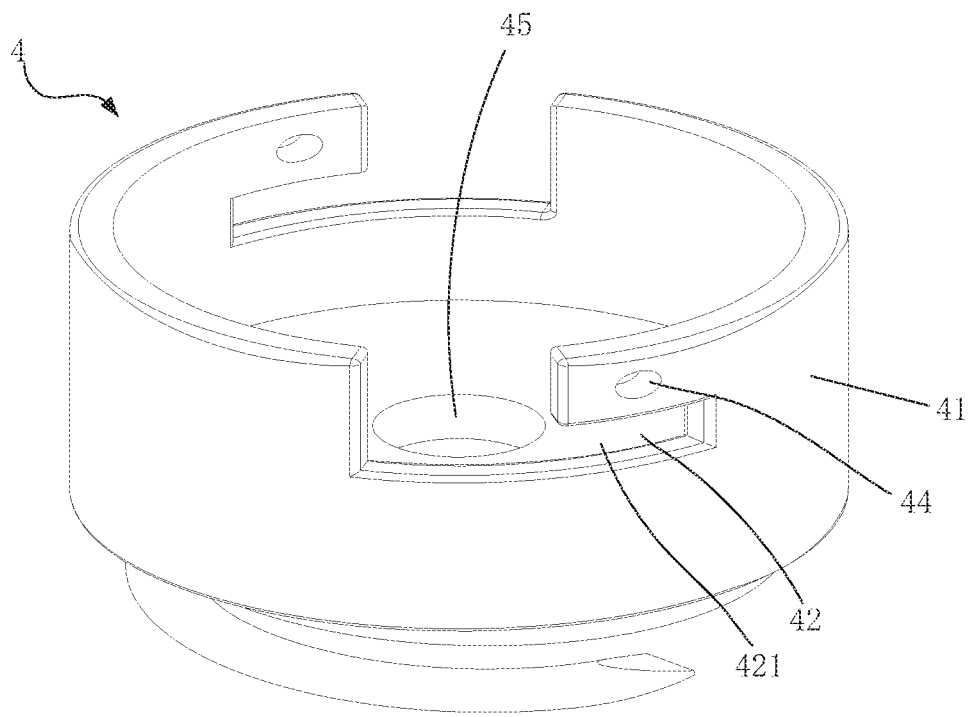
FIG. 6a is a schematic diagram showing the structure of a leading component including a guide socket in Embodiment 2 of the present invention.

As shown in FIG. 6a, the leading component 4 includes a second body 41, and both disposed on the second body 41, the third connecting member 42 and the fourth connecting member. In this embodiment, the third connecting member 42 includes a locating snap recess 421, which is arranged in an outer wall of the second body 41 so as to radially extend through the outer wall. The locating snap recess 421 further extends along a circumference of the second body 41 so that the locating block 321 can be circumferentially snapped and locked therein. Moreover, the locating snap recess 421 is axially open at one side, and the locating block 321 can move into the locating snap recess 421 through the opening. The fourth connecting member include the aforementioned pin hole 44, which radially extends through the outer wall of the second body 41 and is configured to be aligned with the pin hole 34 in the trailing component and allow the locating pin to be inserted therethrough.

The associated biodegradable connecting member include the aforementioned locating pin which is configured to be inserted through both the pin hole 34 in the trailing component 3 and the pin hole 44 in the leading component 4, thus locking the trailing component 3 and the leading component 4 against each other. Preferably, the locating pin is made of a biodegradable material and configured to begin to degrade a predetermined period of time after the leadless pacemaker is implanted into the body.

With combined reference to FIG. 4, in a practical assembly process, the trailing component 3 is distally inserted into a proximally open internal cavity 25 of the leading component 4. During the insertion, the locating block 321 is guided into the locating snap recess 421 through the opening thereof, and the locating block 321 is rotated so as to be moved into and fastened in an arc-shaped slot of the locating snap recess 421. In this way, relative rotational displacement in a first direction between the leading component 4 and the trailing component 3 is limited. After that, the locating pin is inserted successively through the pin holes 34 and 44 in the trailing and leading components 3 and 4, thus establishing a pinned connection between them. In this way, the locating pin limits relative rotational displacement in a second direction between the leading component 4 and the trailing component 3. The first and second directions are opposite to each other. The snap fit and the pinned connection securely lock the trailing component 3 and the leading component 4 against each other and make them inseparable before the locating pin is degraded.

In this embodiment, at least one locating block 321 is provided. Preferably, two locating blocks 321 are arranged on the first body 31 in symmetry with respect to the axis of the first body 31. Also preferably, two pin holes 34, as well as two pin holes 44, are arranged in symmetry in the corresponding body. Of course, also preferably, two locating pins are provided. However, the present invention is not limited to any particular number of pin holes, locating pins or locating blocks, or to any particular location of any pin hole 34 or locating block 321 on the first body 31, or to any particular location of any pin hole 44 or locating snap recess 421 on the second body 41, as long as the locating blocks 321 will not interfere with the insertion of the locating pins. Possible shapes for the locating snap recesses 421 include, but are not limited to, an L-like shape. Further, the present invention is not limited to any particular method of forming the locating pins, and they may be formed either by injection molding or by mechanical machining.

In an alternative embodiment, the locating snap recess 421 may be arranged on the first body 31, and the locating block 321 on the second body 41. The locating snap recess 421 may be arranged on the first body 31 in the same manner as its arrangement on the second body 41, and the locating block 321 may be arranged on the second body 41 in the same manner as its arrangement on the first body 31. Therefore, they need not be described in further detail herein.

Figure 5B:
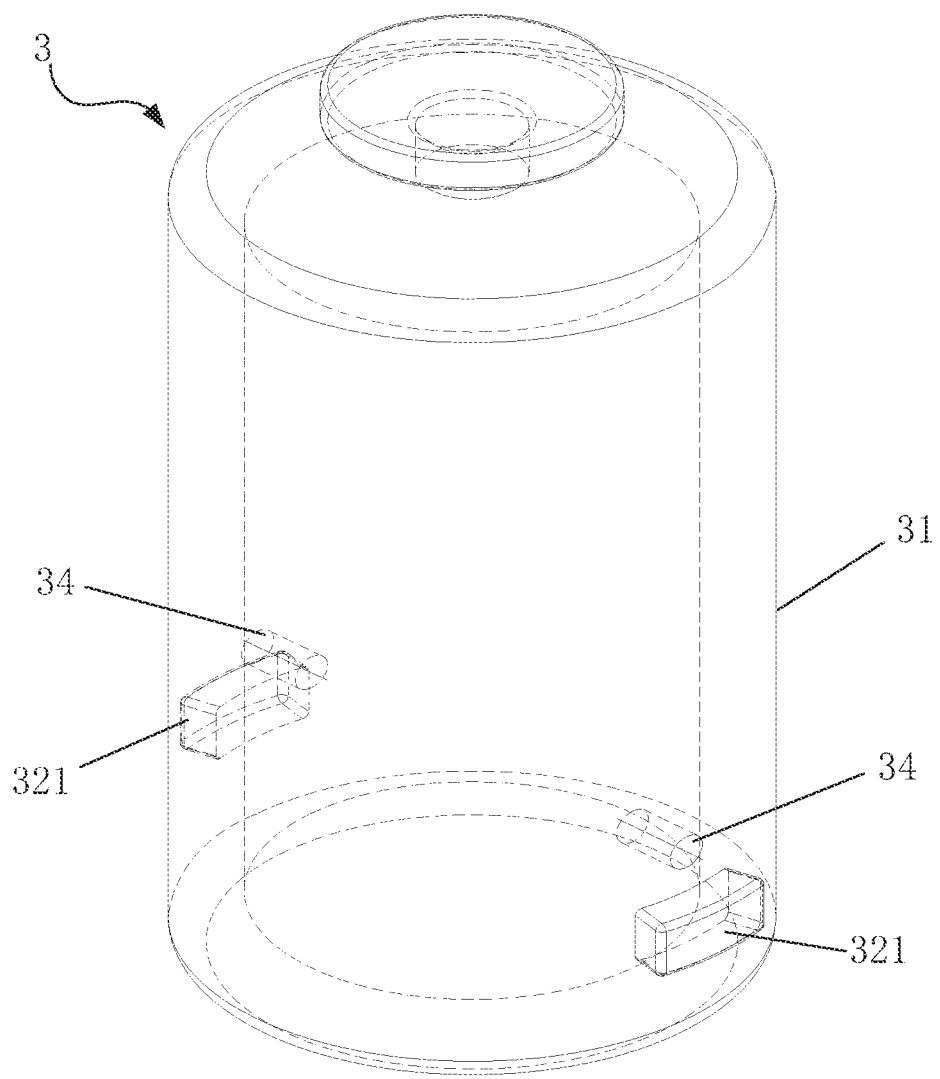
FIG. 5b is a schematic diagram showing the structure of the trailing component not including the guide stud in Embodiment 2 of the present invention.
Figure 6B:
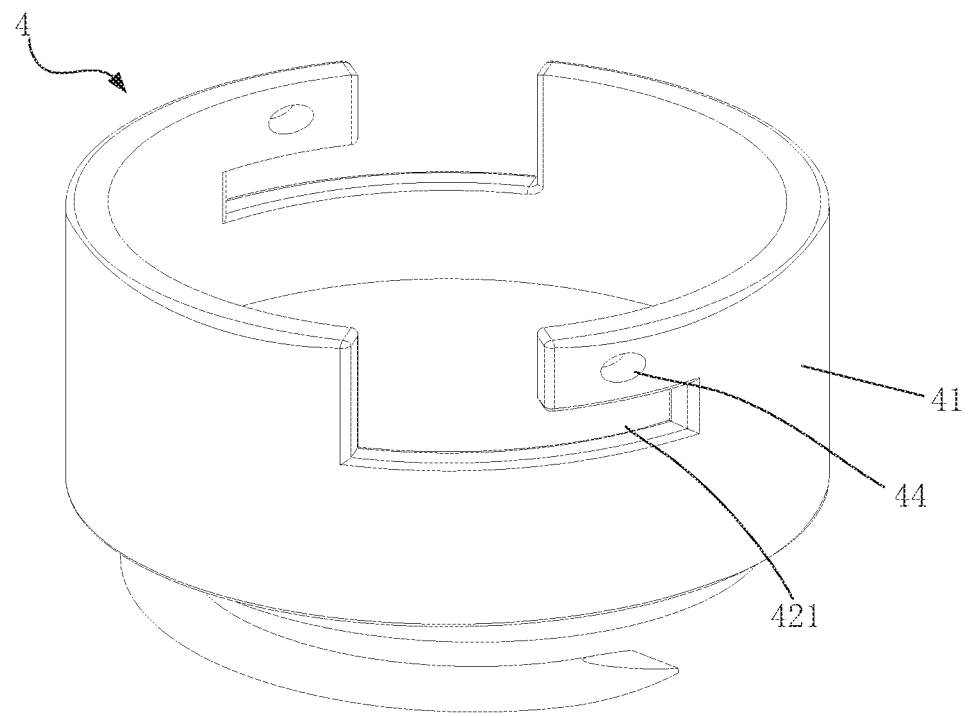
FIG. 6b is a schematic diagram showing the structure of the leading component not including the guide socket in Embodiment 2 of the present invention.

With continued reference to FIG. 5a, in one embodiment, the first body 31 is provided at a distal end thereof with a guide stud 35, and as shown in FIG. 6a, a guide socket 45 is formed at the bottom of the internal cavity 25 of the second body 41. The guide stud 35 is configured to be inserted into the guide socket 45 so as to form a fitted connection therebetween. Of course, an interchanged arrangement is also possible. That is, the guide stud may be instead provided at a proximal end of the second body 41, and the guide socket at a distal end of the first body 31. In this case, the guide stud is also configured to be inserted into the guide socket to form a fitted connection therebetween. Still alternatively, the guide stud and the guide socket may be omitted, and the connection between the leading and trailing components instead only relies on the connection between the locating block 321 and the locating snap recess 421, as shown in FIGS. 5b and 6b. Preferably, the connection between the guide stud 35 and the guide socket 45, or the connection between the locating block 321 and the locating snap recess 421, is also an electrically conductive connection.

In this embodiment, the snap fit between the locating block 321 and the locating snap recess 421 and the connection between the locating pin and the pin hole can ensure that the trailing component 3 and leading component 4 will not be separated from each other during manipulation of the leadless pacemaker 200. Thus, the leadless pacemaker 200 can be adjusted in implantation location or entirely retrieved in the acute phase simply by turning it until an anchoring mechanism 22 at a distal end of the leading component 4 is detached from myocardial tissue. However, when in the chronic phase, the majority or entirety of the leadless pacemaker 100 is wrapped by tissue, making it difficult to be retrieved. In order to reduce the difficulty of retrieval, the locating pin is configured as a biodegradable structure, which when completely degraded, will lose its locking effect. At this point, despite that the pacemaker is mostly or entirely wrapped by tissue, in order to ensure reliable use, the snap fit between the locating block and the locating snap recess still ensures that the trailing component 3 will not just fall off, and a physician can separate it from the leading component 4 simply by turning it using the delivery device. After the separation, the trailing component 3 is retrieved from the body, while the leading component 4 is left therein. It would be understood that, since the locating pin has been degraded, in order to engage a new trailing component 3 with the leading component 4 remaining in the body, it is only necessary to snap the locating block 321 into the locating snap recess 421 without needing to deploy a new locating pin. Of course, it is preferred to entirely implant a brand new leadless pacemaker into the body.

Embodiment 3

This embodiment provides a leadless pacemaker 300, which is essentially similar in structure to that of Embodiment 1. In the following, only differences between them are described.

Figure 7A:
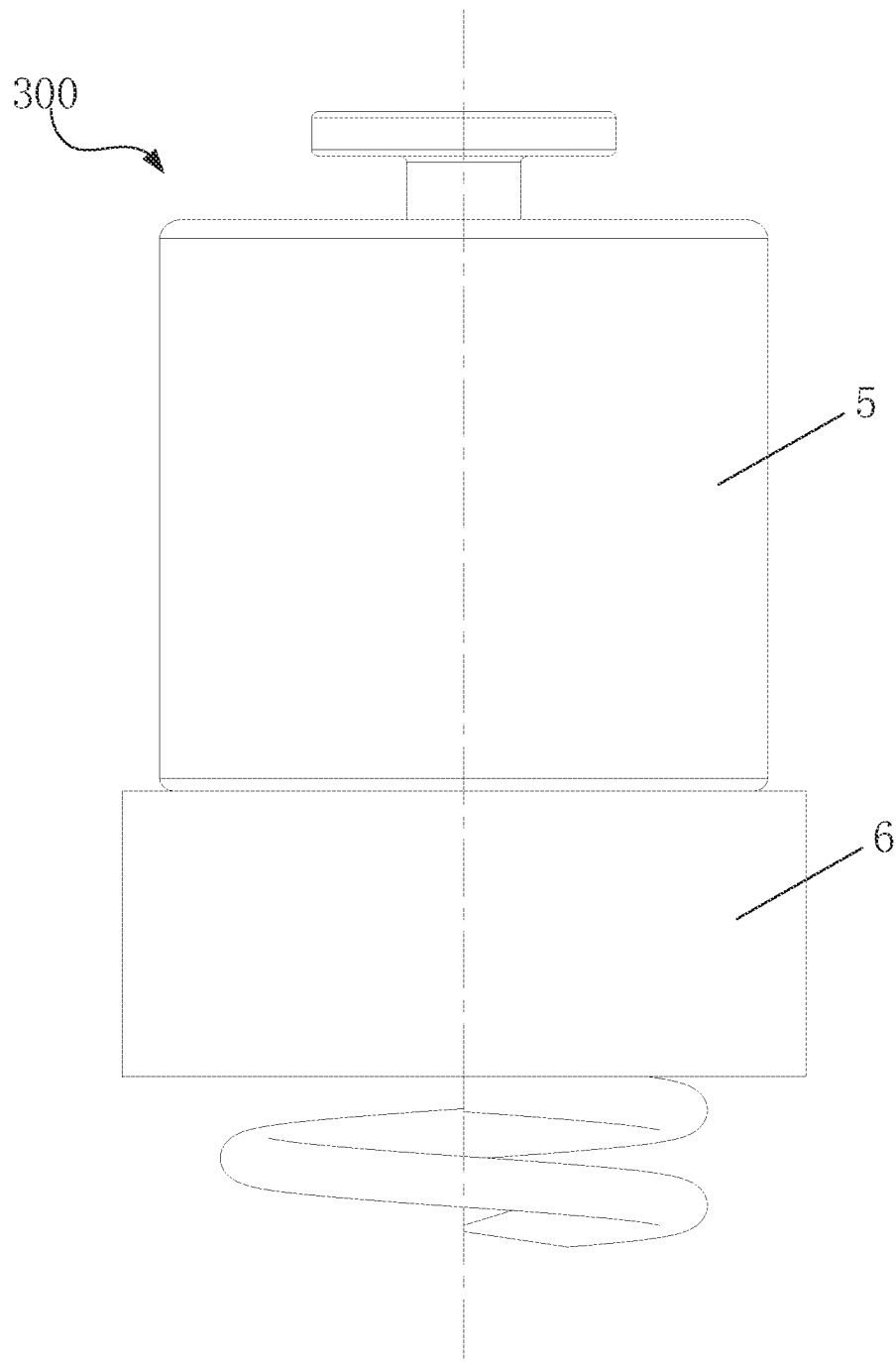
FIG. 7a shows a leadless pacemaker provided in Embodiment 3 of the present invention in an assembled configuration.
Figure 7B:
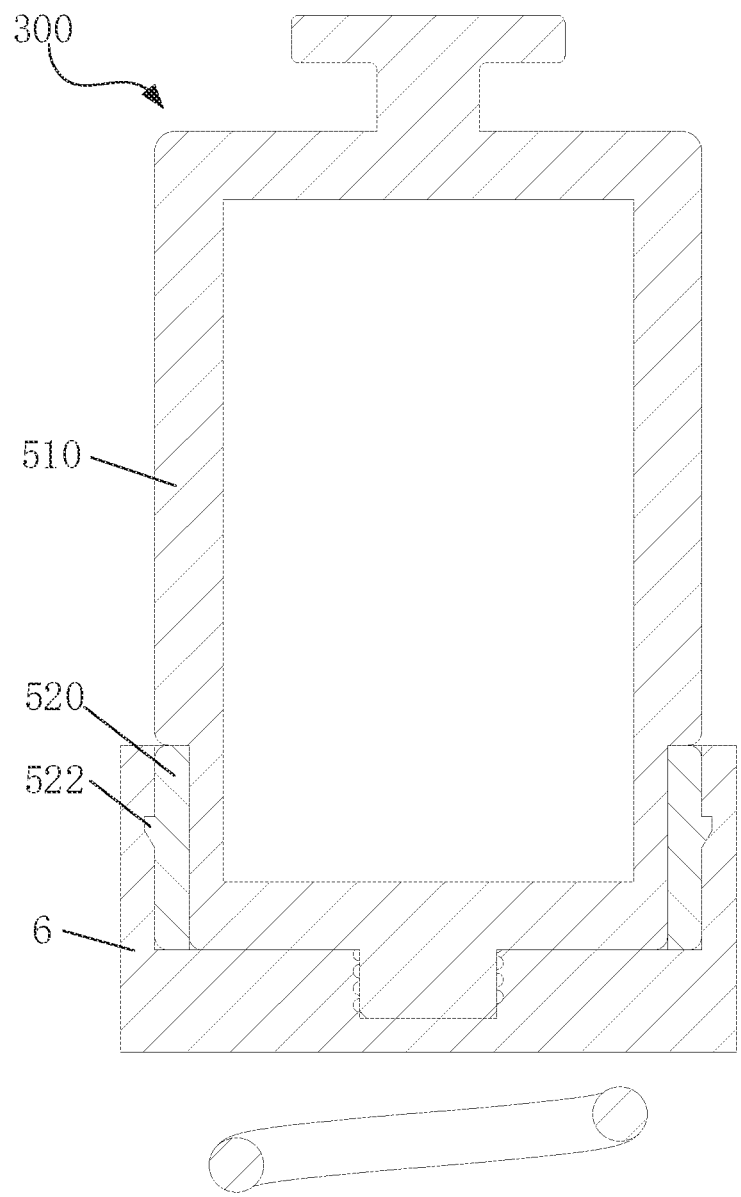
FIG. 7b is an axial cutaway view of the leadless pacemaker in Embodiment 3 of the present invention.
Figure 8A:
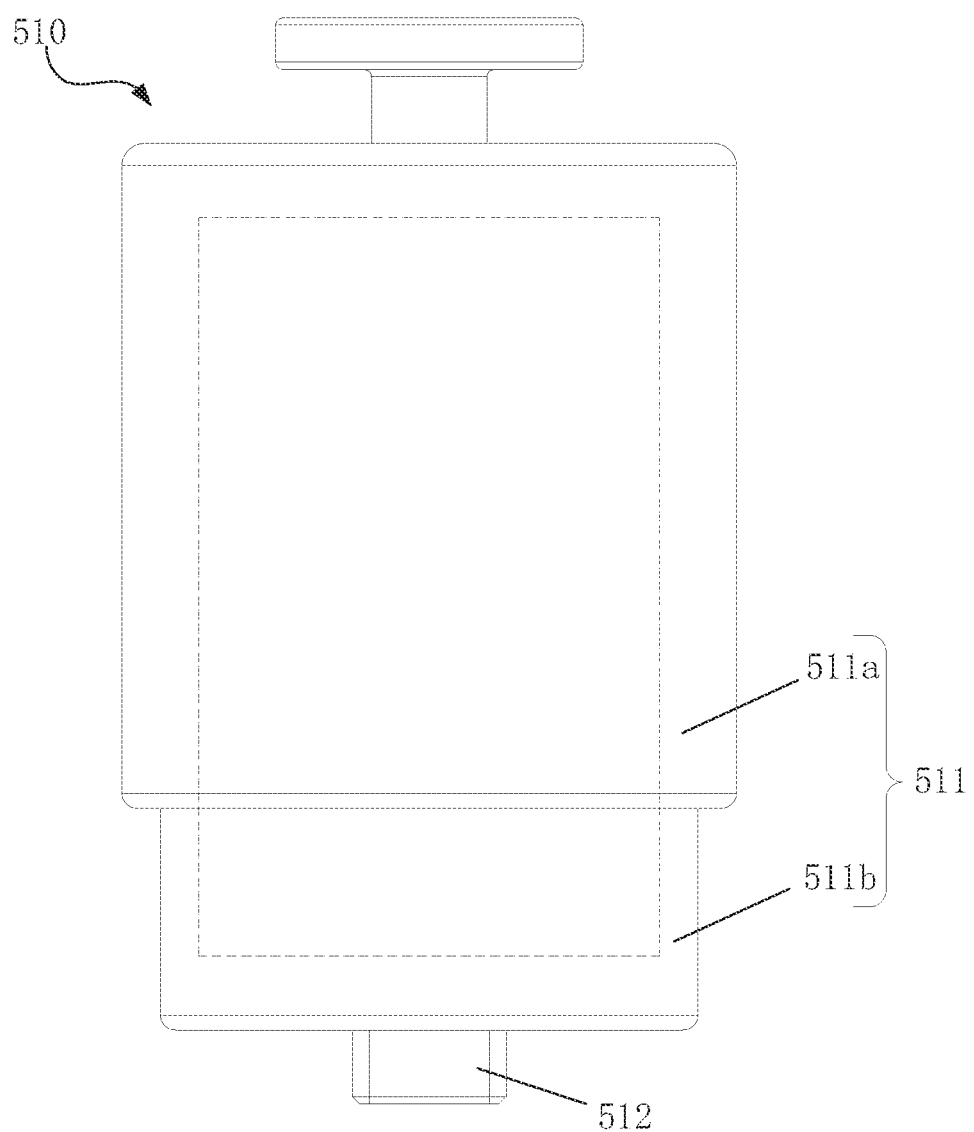
FIG. 8a is a schematic diagram showing the structure of a first part of a trailing component in Embodiment 3 of the present invention.
Figure 8B:
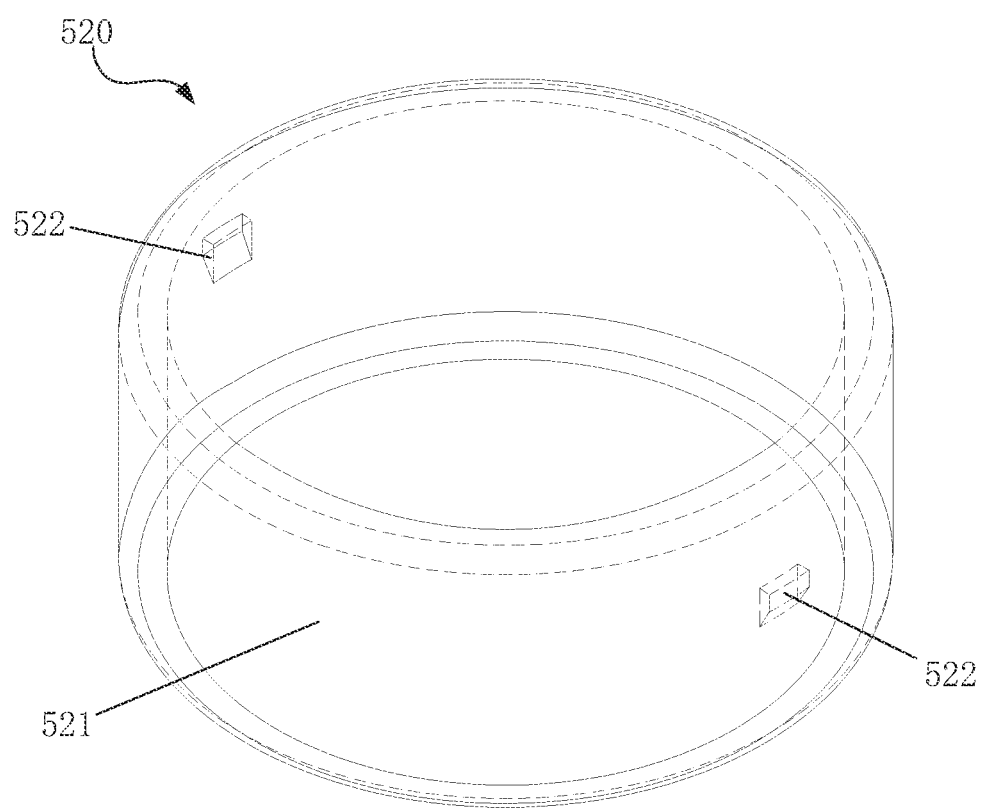
FIG. 8b is a schematic diagram showing the structure of a second part of the trailing component in Embodiment 3 of the present invention.
Figure 8C:
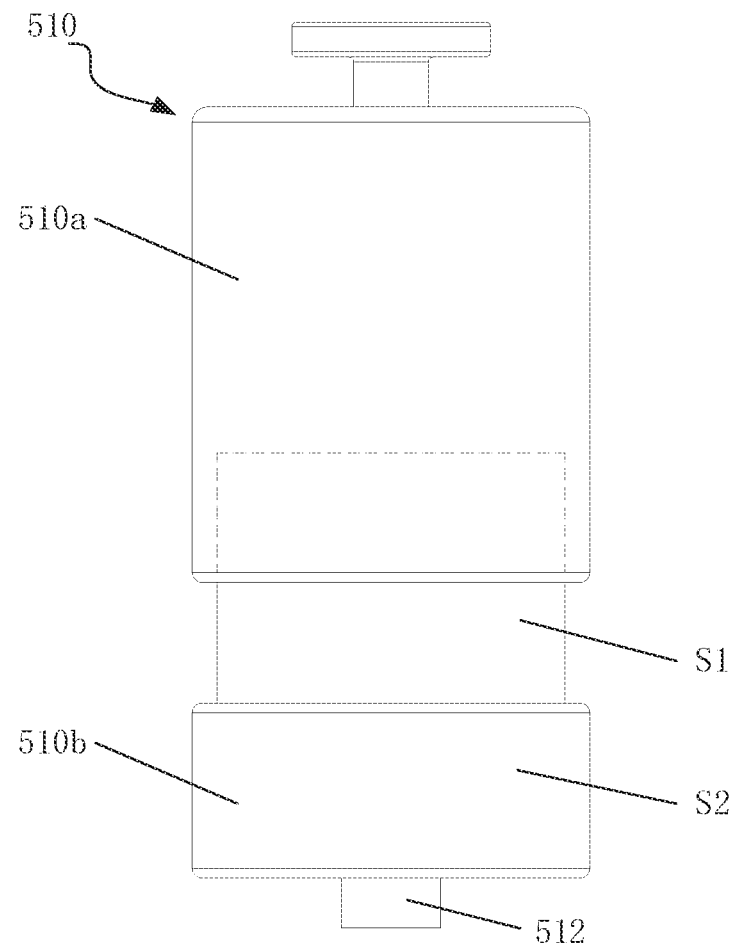
FIG. 8c schematically illustrates another preferred example of the first part in Embodiment 3 of the present invention.
Figure 9:
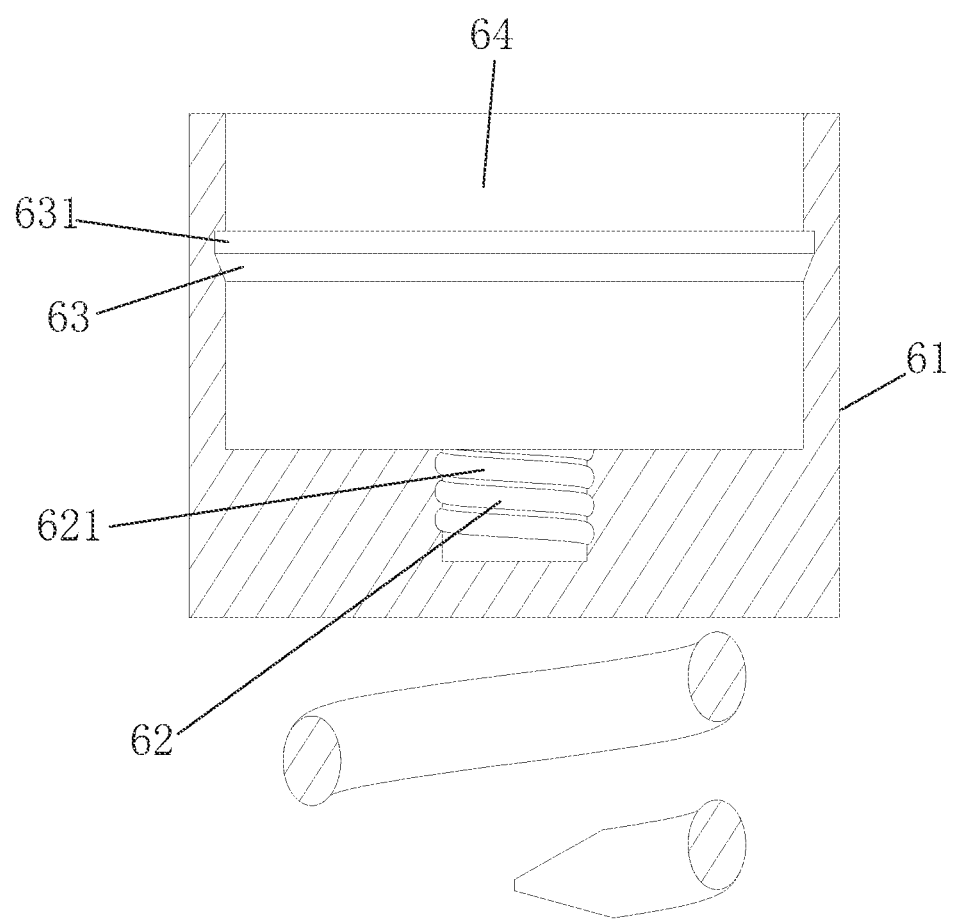
FIG. 9 is an axial cutaway view of a leading component in Embodiment 3 of the present invention.

FIG. 7a schematically illustrates the leadless pacemaker provided in Embodiment 3 of the present invention. FIG. 7b is an axial cutaway view of the leadless pacemaker in Embodiment 3 of the present invention. FIG. 8a is a schematic diagram showing the structure of a first part of a trailing component in Embodiment 3 of the present invention. FIG. 8b is a schematic diagram showing the structure of a second part of the trailing component in Embodiment 3 of the present invention. FIG. 8c schematically illustrates another preferred example of the first part in Embodiment 3 of the present invention. FIG. 9 is an axial cutaway view of a leading component in Embodiment 3 of the present invention.

As shown in FIGS. 7a to 9, the leadless pacemaker 300 provided in the Embodiment 3 of the present invention includes the trailing component 5 and the leading component 6, which are connected both by a snap-fit connection between a second connecting member and a fourth connecting member 63 and by a threaded connection between a first connecting member and a third connecting member 62. One of the second connecting member and the fourth connecting member 63 includes a locating snap recess, and the other of the second connecting member and the fourth connecting member 63 includes a protruding snap feature configured as a ring. In this way, the threaded connection between the first connecting member and the third connecting member 62 is decoupled from circumferential limitation accomplished by the protruding snap feature and the locating snap recess.

As shown in FIGS. 8a and 8b, the trailing component 5 includes a first part 510 and a second part 520. The first part 510 includes a first body 511, the first body 511 includes a main portion 511a and a recessed portion 511b at a distal end of the main portion 511a. An outer diameter of the main portion 511a is greater than an outer diameter of the recessed portion 511b, and the second part 520 is directly disposed over the recessed portion 511b. The second part 520 is a sleeve open at both ends, and an outer diameter of the second part 520 is preferably the same as the diameter of the main portion 511a. The first connecting member is provided on the first part 510, and the second connecting member on the second part 520. In this embodiment, the first connecting member is a guide stud 512, the guide stud 512 has an external thread and provided at a distal end of the recessed portion 511b. Further, the second connecting member is a barbed fastener 522.

Referring to FIG. 8b, in conjunction with FIG. 7b, the second part 520 includes a third body 521, and the barbed fastener 522 extends outwardly from an outer wall of the third body 521. The present invention is not limited to any particular shape of the barbed fastener 522, and possible shapes include, but are not limited to, triangular, trapezoidal and other shapes. Further, at least two barbed fasteners 522 may be provided preferably in symmetry.

As shown in FIG. 9, the leading component 6 includes a second body 61, and both provided on the second body 61, the third connecting member 62 and the fourth connecting member 63. In this embodiment, the third connecting member 62 includes a guide socket 621 threadedly engageable with the guide stud 512. Preferably, the guide socket 621 is electrically connected to the guide stud 512. The fourth connecting member 63 includes the locating snap recess 631 that is engageable with the barbed fastener 522. The locating snap recess 631 is implemented as an annular groove formed in a side wall of a proximal internal cavity 64. Further, the guide socket 621 is provided at a center of the bottom of the internal cavity 64.

With combined reference to FIG. 7b, during a practical assembly process, the second part 520 is first disposed over the recessed portion of the first part 510, and the two are connected together by, without limitation, adhesive bonding, welding, a hot-melt connection, an interference fit or the like. Subsequently, the leading component 6 is disposed over the second part 520 and turned so that the guide stud 512 and the guide socket 621 are tightly threadedly engaged with each other and, at the same time, the barbed fastener 522 on the second part 520 gradually moves into the locating snap recess on the leading component 6 until it is tightly locked therein. In this way, the trailing component 5 and the leading component 6 are locked against each other.

According to embodiments of the present invention, the barbed fastener 522 can be separately degraded, while the second part 520 is non-degradable. Alternatively, both the barbed fastener 522 and the second part 520 are degradable. That is, both the second part 520 and the barbed fastener 522 are made of a biodegradable material, and the two may be integrally formed, making the entire component degradable. In some other examples, the locating snap recess may be provided on the second part 520 of the trailing component 5, with the barbed fastener engageable with the locating snap recess on the second part 520 being accordingly provided on the side wall of the internal cavity 64 of the leading component 6. Optionally, one or both of the second part 520 and the barbed fastener may be degradable. When the second part 520 is degradable, the locating snap recess can disappear with the degradation. As a result, the barbed fastener will lose its limiting effect, thus releasing the interlocked second and fourth 63 connecting members.

Thus, in this embodiment, the snap fit between the barbed fastener 522 and the locating snap recess 631 and the threaded engagement between the guide stud 512 and the guide socket 321 can ensure that the trailing component 5 and leading component 6 will not be separated from each other during manipulation of the leadless pacemaker 300. Therefore, the leadless pacemaker 300 can be adjusted in implantation location or entirely retrieved in the acute phase simply by turning it until an anchoring mechanism at a distal end of the leading component 6 is detached from myocardial tissue. However, when in the chronic phase, the majority or entirety of the leadless pacemaker 100 is wrapped by tissue, making it difficult to be retrieved. In order to reduce the difficulty of retrieval, the barbed fastener 522 and/or second part 520 is/are configured as biodegradable structure(s), which when completely degraded, will lose the locking effect of the barbed fastener. At this point, despite that the pacemaker is mostly or entirely wrapped by tissue, in order to ensure reliable use, the threaded engagement between the guide stud and the guide socket still ensures that the trailing component 5 will not just fall off, and a physician can separate it from the leading component 5 simply by turning it using the delivery device. After the separation, the trailing component 5 is retrieved from the body, while the leading component 6 is left therein.

Further, the first part 510 may be either an integral part or an assembly of two subparts. As shown in FIG. 8c, the first part 510 is an assembly of two subparts: a first subpart 510a and a second subpart 510b. The second subpart 510b preferably includes a first portion S1 and a second portion S2. An outer diameter of the first portion S1 is smaller than an outer diameter of the second portion S2. During practical assembly, the first portion S1 is inserted into the first subpart 510*a* and fixedly connected thereto preferably by a means having good sealing properties, such as a threaded connection, a snap fit or the like, thereby forming the first part 510 as shown in FIG. 8*c*. Part of the first portion S1 that is exposed out of the first subpart 510*a* forms the aforementioned recessed portion adapted for disposal of the second part 520 thereon and hence firm retention of the second part 520 between the first subpart 510*a* and the second subpart 510*b*. Preferably, the outer diameter of the second portion S2 is equal to an outer diameter of the first subpart 510*a*, and the outer diameter of the second part 520 is also equal to the outer diameter of the first subpart 510*a*.

Although a few preferred embodiments of the present invention have been described above, the invention is not limited to the scope of the embodiments disclosed hereinabove. For example, apart from the aforementioned snap fit, pinned connection and the like, the connection between the second connecting member of the trailing component and the fourth connecting member of the leading component may also be accomplished by a riveted connection or the like. In addition, the present invention is not limited to any particular method of establishing the electrical connection between the trailing and leading components. In addition, in the leadless pacemakers provided in the embodiments of the present invention, it is possible that the second connecting member of the trailing component is degradable, or that the fourth connecting member of the leading component is degradable, or that both the second connecting member of the trailing component and the fourth connecting member of the leading component are degradable, or that the second connecting member is fitted and connected to the fourth connecting member by an associated biodegradable connecting member. Further, although the protruding snap feature such as the elastic fastener, locating block or barbed fastener on the leading component is not shown herein, on the basis of the disclosure of this application, one skilled in the art will know how to arrange the protruding snap feature on the leading component and how the protruding snap feature is biodegraded to unlock the locating snap recess of the trailing component.

Finally, with combined reference to FIG. 10, manipulation of the leadless pacemaker 100 of Embodiment 1 will be further described below to exemplify manipulation of the leadless pacemakers (100, 200 and 300) provided in the embodiments of the present invention.

As shown in FIG. 10, during implantation, the physician may introduce a guidewire through the inferior vena cava and deliver a guide sheath over the guidewire into the heart (e.g., a ventricle or atrium), followed by withdrawal of the guidewire. Subsequently, the locating sheath 400 and shrinkable sheath 500 in which the leadless pacemaker is loaded in a consolidated configuration (where the fifth connecting member 14 at the proximal end of the leadless pacemaker is connected to the shrinkable sheath 500) may be delivered together over the guide sheath into the heart. In this process, the operator may manipulate the locating sheath 400 with the aid of an X-ray imaging device so as to position the locating sheath 400 at an appropriate location (which can be determined by the physician at his/her own discretion). After the locating sheath 400 is retained at the location, the shrinkable sheath 500 may be manipulated to cause the anchoring mechanism 22 on the leading component 2 to rotate and pierce myocardial tissue, thus achieving anchoring of the leadless pacemaker. At last, the shrinkable sheath, the locating sheath, the guide sheath and other delivery components may be withdrawn, ending the leadless pacemaker implantation process.

Further, when it is needed to retrieve the leadless pacemaker or adjust its location, the physician may again introduce the guidewire and deliver the guide sheath over the guidewire. After the guidewire is withdrawn, the locating sheath 400 may be delivered into the heart using the guide sheath and further advanced to the location of the leadless pacemaker (with the aid of X-ray imaging). After that, the shrinkable sheath 500 may be slowly advanced in the locating sheath until it comes into connection with the fifth connecting member 14 of the leadless pacemaker. Following this, with the leadless pacemaker being held stationary, the locating sheath 400 may be pushed forward so that the leadless pacemaker is slowly retrieved into the locating sheath 400, and the entire leadless pacemaker may be rotated to detach the helical structure from the myocardial tissue. At last, the shrinkable sheath, the locating sheath, the guide sheath and other delivery components may be withdrawn, ending the leadless pacemaker retrieval process.

Furthermore, when it is needed to retrieve or replace the leadless pacemaker in the chronic phase, similarly, the physician may again introduce the guidewire and deliver the guide sheath over the guidewire. After the guidewire is withdrawn, the locating sheath may be delivered into the heart using the guide sheath and further advanced to the location of the leadless pacemaker (with the aid of X-ray imaging). After that, the shrinkable sheath 500 may be inserted into the locating sheath 400 and moved into connection with the fifth connecting member 14 of the trailing component 1. Following this, with the leadless pacemaker being held stationary, the locating sheath may be pushed forward so that the trailing component of the leadless pacemaker is retrieved into the locating sheath (at this point, the proximal end face 26 of the leading component 2 limits the locating sheath 400 so that the locating sheath 400 can be pushed only to the proximal end of the leading component). Afterward, the leading component 4 may be retained stationary using the locating sheath 400, and the shrinkable sheath 500 may be then rotated to cause the trailing component 1 to rotate to disengage itself from the leading component 2. At last, the trailing component 1 may be withdrawn together with the locating sheath 400 from the human body.

In summary, in the leadless pacemaker and the trailing and leading components thereof provided in the present invention, the trailing component includes first and second connecting members and the leading component includes third and fourth connecting members. The first connecting member is configured to be detachably connected to the third connecting member, and the second connecting member is configured to be detachably or non-detachably connected to the fourth connecting member, thus locking the trailing and leading components against each other. Moreover, both the first and third connecting members are non-biodegradable, and at least one of the second and fourth connecting members is biodegradable. Alternatively, the second and fourth connecting members are fitted and connected to each other by an associated biodegradable connecting member. Thus, before the connecting member is degraded, it can be ensured that the trailing and leading components are firmly connected together by the four connecting members, facilitating overall retrieval or adjustment of the pacemaker. Moreover, after the connecting member is degraded, the trailing component can be easily retrieved.

The description presented above is merely that of a few preferred embodiments of the present invention and is not intended to limit the scope thereof in any sense. Any and all changes and modifications made by those of ordinary skill in the art based on the above teachings fall within the scope as defined in the appended claims.

What is claimed is:

1. A trailing component of a leadless pacemaker for use with a leading component of the leadless pacemaker, the trailing component comprising a first connecting member and a second connecting member,
    wherein the first connecting member is configured to be detachably connected to the leading component and the second connecting member is configured to be non-detachably or detachably connected to the leading component, thereby achieving interlocking between the trailing component and the leading component, and wherein the first connecting member is non-biodegradable and the second connecting member is biodegradable, or the second connecting member is fitted and connectable to the leading component by an associated biodegradable connecting member.

2. The trailing component of a leadless pacemaker according to claim 1, wherein the second connecting member is configured to be connected to the leading component by a snap fit or by a pinned connection.

3. The trailing component of a leadless pacemaker according to claim 2, wherein the second connecting member comprises a pin hole in alignment with a pin hole in the leading component and configured for insertion of a biodegradable locating pin therethrough.

4. The trailing component of a leadless pacemaker according to claim 2, wherein the second connecting member comprises a locating snap recess configured to form a snap fit with a protruding snap feature of the leading component; or wherein the second connecting member comprises a protruding snap feature made of a biodegradable material and configured to form a snap fit with a locating snap recess of the leading component and begin to be degraded a predetermined period of time after the leadless pacemaker is implanted.

5. The trailing component of a leadless pacemaker according to claim 1, wherein the first connecting member is configured to be connected to the leading component by a threaded connection, a snap fit or an interference fit.

6. The trailing component of a leadless pacemaker according to claim 5, wherein the first connecting member comprises a guide socket configured for fitted engagement with a guide stud of the leading component, or wherein the first connecting member comprises a guide stud configured for fitted engagement with a guide socket of the leading component.

7. The trailing component of a leadless pacemaker according to claim 6, wherein the guide socket has an internal thread, or wherein the guide stud has an external thread.

8. The trailing component of a leadless pacemaker according to claim 5, wherein the first connecting member comprises a locating snap recess configured to form a snap fit with a protruding snap feature of the leading component, or wherein the first connecting member comprises a protruding snap feature configured to form a snap fit with a locating snap recess of the leading component.

9. The trailing component of a leadless pacemaker according to claim 1, wherein the trailing component comprises a first part and a second part, the first part comprising a main portion and a recessed portion, the second part disposed over the recessed portion, and wherein the second connecting member is provided on the second part and the second connecting member and/or the second part is/are biodegradable.

10. The trailing component of a leadless pacemaker according to claim 9, wherein an outer diameter of the second part is equal to an outer diameter of the main portion.

11. A leading component of a leadless pacemaker for use with a trailing component of the leadless pacemaker, the leading component comprising a third connecting member and a fourth connecting member,
    wherein the third connecting member is configured to be detachably connected to the trailing component and the fourth connecting member is configured to be non-detachably or detachably connected to the trailing component, thereby achieving interlocking between the trailing component and the leading component, and wherein the third connecting member is non-biodegradable and the fourth connecting member is biodegradable, or the fourth connecting member is fitted and connectable to the trailing component by an associated biodegradable connecting member.

12. The leading component of a leadless pacemaker according to claim 11, wherein the fourth connecting member is configured to be connected to the trailing component by a snap fit or by a pinned connection.

13. The leading component of a leadless pacemaker according to claim 12, wherein the fourth connecting member comprises a pin hole in alignment with a pin hole in the trailing component and configured for insertion of a biodegradable locating pin therethrough-; or wherein the fourth connecting member comprises a locating snap recess configured to form a snap fit with a protruding snap feature of the trailing component; or
    wherein the fourth connecting member comprises a protruding snap feature made of a biodegradable material and configured to form a snap fit with a locating snap recess of the trailing component and begin to be degraded a predetermined period of time after the leadless pacemaker is implanted.

14. The leading component of a leadless pacemaker according to claim 11, wherein the third connecting member is configured to be connected to the trailing component by a threaded connection, a snap fit or an interference fit.

15. The leading component of a leadless pacemaker according to claim 14, wherein the third connecting member comprises a guide socket configured for fitted engagement with a guide stud of the trailing component, or wherein the third connecting member comprises a guide stud configured for fitted engagement with a guide socket of the trailing component.

16. The leading component of a leadless pacemaker according to claim 15, wherein the guide socket has an internal thread, or wherein the guide stud has an external thread.

17. The leading component of a leadless pacemaker according to claim 14, wherein the third connecting member comprises a locating snap recess configured to form a snap fit with a protruding snap feature of the trailing component, or wherein the third connecting member comprises a protruding snap feature configured to form a snap fit with a locating snap recess of the trailing component.

18. A leadless pacemaker comprising:
    a trailing component comprising a first connecting member and a second connecting member; and a leading component configured to be secured to a predetermined object, the leading component comprising a third connecting member and a fourth connecting member, wherein the first connecting member is detachably connected to the third connecting member and the second connecting member is non-detachably or detachably connected to the fourth connecting member, thereby achieving interlocking between the trailing component and the leading component, and wherein the first and third connecting members are non-biodegradable, and the second connecting member and/or the fourth connecting member is/are biodegradable, or the second connecting member is fitted and connected to the fourth connecting member by an associated biodegradable connecting member.

19. The leadless pacemaker according to claim 18, wherein the first connecting member is threadedly connected to the third connecting member, wherein the second connecting member is connected to the fourth connecting member by a snap fit, and wherein one of the second and fourth connecting members comprises a locating snap recess, and the other one of the second and fourth connecting members comprises a protruding snap feature, the locating snap recess configured in an annular shape.

20. The leadless pacemaker according to claim 18, wherein each of the second and fourth connecting members comprises a pin hole, and the pin hole in the trailing component is aligned with the pin hole in the leading component, wherein the associated biodegradable connecting member comprises a locating pin inserted through both the pin holes of the trailing and leading components and configured to begin to be degraded a predetermined period of time after the leadless pacemaker is implanted.

* * * * *